US006944323B1

United States Patent
Parani et al.

(10) Patent No.: US 6,944,323 B1
(45) Date of Patent: Sep. 13, 2005

(54) DEVICE FOR DETECTING FOREIGN SUBSTANCES IN A THREAD

(75) Inventors: Peter Parani, Grüt/Gossau (CH); Hans Wampfler, Zürich (CH)

(73) Assignee: Uster Technologies AG, Uster (CH)

( * ) Notice: Subject to any disclaimer, the term of this patent is extended or adjusted under 35 U.S.C. 154(b) by 0 days.

(21) Appl. No.: 09/806,439

(22) PCT Filed: Sep. 27, 1999

(86) PCT No.: PCT/CH99/00458

§ 371 (c)(1),
(2), (4) Date: Mar. 30, 2001

(87) PCT Pub. No.: WO00/20849

PCT Pub. Date: Apr. 13, 2000

(30) Foreign Application Priority Data

Oct. 1, 1998 (CH) .................................... 1994/98

(51) Int. Cl.⁷ .............................................. G06K 9/00

(52) U.S. Cl. ...................................... 382/141; 382/111

(58) Field of Search ............. 382/141, 111; 356/237.1, 356/238.1, 238.2, 242.1; 700/130, 144; 348/86, 348/88, 125, 128; 250/559.4; 112/278

(56) References Cited

U.S. PATENT DOCUMENTS

| 4,739,176 A | 4/1988 | Allen et al. |
| 4,893,223 A | 1/1990 | Arnold |
| 5,161,475 A * | 11/1992 | Tawara et al. ............... 112/278 |
| 5,345,515 A | 9/1994 | Nishi et al. |
| 5,499,794 A | 3/1996 | Aeppli |

FOREIGN PATENT DOCUMENTS

| CH | 683293 | 2/1994 |
| DE | 39 28 279 | 2/1991 |
| DE | 41 31 664 | 3/1993 |
| EP | 0 385 262 | 9/1990 |
| EP | 0 761 585 | 3/1997 |

* cited by examiner

Primary Examiner—Vikkram Bali
(74) Attorney, Agent, or Firm—Burns, Doane, Swecker & Mathis, L.L.P.

(57) ABSTRACT

The invention relates to a device for detecting foreign substances in a thread using a detector which line-scans the thread, the latter being lit by an illumination element. The aim of the invention is to provide a means of continuously testing the thread with good resolution and at a high speed. To this end, the inventive device consists of a compact unit made up of a sensor or a detector, an objective and an illumination element. These elements have a common axis and the illumination element enables the thread to be illuminated with a very high light intensity. To this end, the illumination element (1) is hemispherical and has light sources which are distributed across the hemisphere (5).

7 Claims, 1 Drawing Sheet

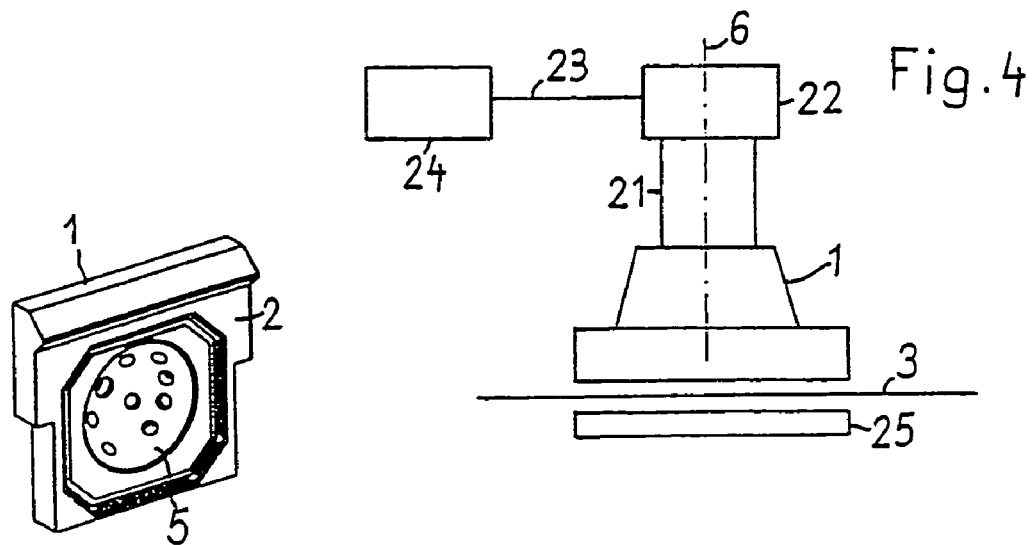
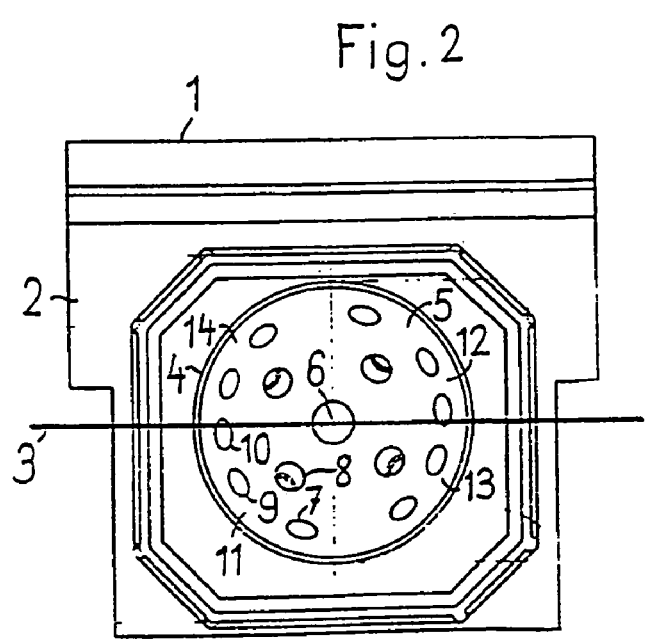
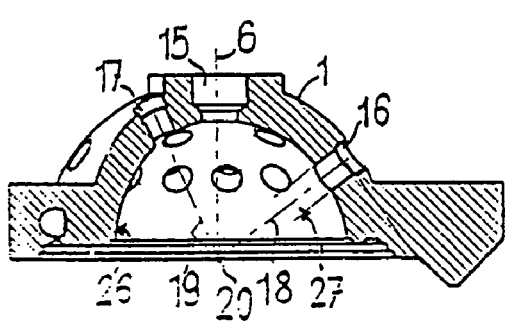

DEVICE FOR DETECTING FOREIGN SUBSTANCES IN A THREAD

The invention relates to a device for detecting foreign substances in a thread with the aid of a detector which line-scans the thread which is lit by an illumination element.

A device of this type is known, for example, from DE 41 31 664 in which the thread is wound onto two rollers in such a way that a layer with a plurality of adjacent portions of the same thread develops. Arranged on one side of this layer is a light source and on the other side is a camera connected to a computer which stores an image processing programme. In this process, the camera produces an image of the layer in which foreign substances such as husk parts can be recognised according to their structure, in each case, and can be counted. By rotating the rollers, the layer can be displaced far enough for adjacent portions of the thread to be moved into the view of the camera. In this way, the whole length of a thread sample can be gradually detected and examined.

The disadvantage of the device mentioned is that it can only operate discontinuously and with limited speed. This is because the thread should be stationary for producing an image. The device mentioned also needs much space and cannot be integrated into existing thread testers, known per se, provided for other tests on the thread.

Further devices with which these foreign substances can be recognised are known from DE 39 28 279 and U.S. Pat. No. 5,345,515. However, they do not do this in the thread but in a bonded fibre which is a preliminary stage in thread production such as in a fleece or a tape. For this purpose, the tape or fleece is stretched width-wise and pressed flat so only a thin layer remains, revealing all the foreign substances for external observation. These devices also operate slowly and require an alteration in the material being tested. No non-destructive tests are therefore possible.

The invention as characterised in the claims achieves the object of creating a device of the type mentioned in which the thread can be continuously tested, non-destructively, with good resolution and at high speed.

This is achieved according to the invention in that a compact unit consisting of a sensor or detector, a lens and an illumination element is formed, these elements having a common axis and the illumination element allowing illumination of the thread with very high intensity of light. For this purpose, the illumination element is hemispherical in design and has light sources distributed over the hemisphere which predominantly project their light beams directly onto the centre of the hemisphere. The thread is in the centre, or, more precisely, thread is moved through the centre and a portion of the thread depicted on the detector is positioned at least in the region of this centre for the moment when the picture is shot.

The advantages achieved by the invention are particularly seen in the fact that the device according to the invention can be very space-saving in design and as such can be used as part of existing equipment for testing threads. As the device is no longer to recognise foreign substances in a two-dimensional search field, but scans the thread only along its length, a comparative observation of the thread is made in a single dimension, its length. Thus the test is freed from influences which could derive from other adjacent thread portions. There is therefore a neutral detection of the thread with its possible foreign substances which, due to their shape or colour, come only from that thread portion in which they are also contained. Due to the intensive illumination, the thread can be moved at high speed and, despite that, a useful signal can be detected.

The invention is described in more detail with the aid of the examples and with reference to the accompanying drawings, in which:

FIG. 1 shows a part of the device according to the invention in perspective view, FIG. 2 shows the part in plan view, FIG. 3 is a section of the part and FIG. 4 is a schematic view of the whole device.

FIG. 1 shows an illumination element 1 with an end face 2 and a hemisphere 5 in which are arranged openings for light sources.

FIG. 2 shows the illumination element 1 which is spherical-symmetrical internally, with its end face 2, which is flat here, to which a thread 3 is guided, parallel and with spacing, and is moved in its longitudinal direction in a manner known per se. The base circle 4 of a hemisphere 5, the axis of symmetry 6 of which extends perpendicular to the drawing plane, can be seen. The hemisphere 5 has, in a sector 11, a plurality of openings 7, 8, 9, 10 into which light sources in the form of light-emitting diodes, light guides etc. are inserted. The hemisphere 5 has a further sector 12 with the same distribution of openings and sectors 13, 14 with different, but the same as one another, distribution of the openings. As can be seen particularly for the opening 10, these are preferably arranged in such a way that no opening is covered by the thread 3. This measure avoids a disadvantageous shadow being thrown by the thread 3. In the axis of symmetry 6, there is an opening 15 for a detector or an optical system displayed on the detector. The hemisphere 5 preferably has a white-coloured coating facing the thread 3 which promotes multiple reflections of the light and thus produces strong but diffuse illumination of the thread.

FIG. 3 shows the illumination element 1 in section with the axis of symmetry 6 and the opening 15 for the detector or an optical system displayed on the detector and openings 16, 17 for light sources, the axes 18, 19 of which intersect in a centre 20 with the axis of symmetry. It is provided that the axes of the other openings shown also intersect in the centre 20. The illumination element 1 consists of non-transparent material. It extends, on one side, transversely over the thread and, on the other side, along the thread. This also applies in particular, to the cavity 27. Instead of a hemisphere, as shown here, the illumination element 1 can also have an inner face 26 which deviates therefrom. It is, however, like face 26 here, always directed towards the thread 3 and limits a cavity 27 adjacent to the thread 3 with openings for light sources etc. This face 26 could also, for example, have an oval or a cylindrical shape. The arrangement of the light sources is, however, important and these should all be substantially directed towards the centre 20.

FIG. 4 shows the entire device with the illumination element 1, the thread 3 and the axis of symmetry 6. Arranged along this axis of symmetry 6 there is also a lens 21 and a detector 22 which is connected via a bus or a line 23 to the computer 24. A field with sensor elements arranged in lines or a CCD camera is preferably provided as a detector. The lens 21 reduces the image of the thread, for example in a ratio of 1:4, so relatively small sensor elements, for example with dimensions of 0.06 mm×0.015 mm can be worked with. With these dimensions, a husk part with a diameter of approximately 0.5 mm covers the narrow side of a detector element completely. The computer 24 has programmes which allow it to filter the signals from the detector and make comparisons with predetermined threshold values to recognise foreign substances present and to store the number and sizes of the foreign substances. Remote from the illumination element there is also arranged, as background for the thread, a cover 25, of which the side facing the illumination element 1 can have a selectable, preferably white, colour. The hemisphere 5, towards the thread 3, can be closed off by a glass cover to avoid soiling in the openings 7, 8, 9, 10 etc. In a particular embodiment, the cover 25 could also be hemispherical in design and optionally be provided with openings for light sources. If, for example, dark foreign substances are to be recognised in a light-coloured thread, the background, i.e. the cover 25, is also light in colour. This promotes the desired multiple reflections of the light between the illumination element 1 and the cover 25.

The mode of operation of the device according to the invention is as follows:

The thread 3 is moved past the centre 20 of the device at a speed, for example, of 400 m per minute and lit very intensively by the light sources in the openings 7, 8, 9, 10 and corresponding openings in the other sectors 12, 13, 14 with impinging light which partially reflects in the main axis 6 and can be detected by the detector 22. In this way a particularly bright and homogenously illuminated central region is created in the direct vicinity of the centre 20. This can be limited in its extent by apertures in front of the detector 22 or by the dimension of the detector elements or, for example, can also be directed in such a way that it extends further along the thread 3 than transverse to the thread 3. A very small resolution can thus be achieved. Blue light is preferably used, as transmitted, for example, by elements known per se such as LED's (light emitting diodes), lasers etc. This has the advantage that good contrasts to vegetable foreign substances in the thread are produced as these are often brownish, yellowish or redish in colour. A foreign body present in the thread 3 which stands out due to its size exceeding the diameter of the thread, or its colour deviating from the colour of the thread, alters the intensity of the reflected light which is detected by the detector 22. Due to the intensive illumination of the thread in the region of the centre 20 and the sensor element dimensions selected in the detector 22, a high resolution can be achieved which in turn allows the thread to attain high speeds. With a wavelength of 470 nm and an object-to-image ratio of 4:1 and a numerical aperture of 0.08 (on the object side) to the receiver, a power density of 1.8 MW/CM2 is achieved. Evaluation of the signals as produced by the detector 22, is known per se and described, for example, in U.S. Pat. No. 5,499,794.

What is claimed is:

1. A device for detecting foreign substances in a thread, comprising:
    an illumination element that intensively illuminates a thread moving in a longitudinal direction, said illumination element having an end face that defines a plane parallel to said thread, a cavity in said end face having a hemisphere-shaped inner surface that faces said thread, and openings in said surface with light sources; and
    a detector disposed on an axis of symmetry extending through the center of the hemisphere defined by said inner surface, for scanning the thread.

2. The device of claim 1, wherein the thread moves perpendicular to said axis of symmetry.

3. The device of claim 1, wherein the axis of each of said openings intersects said axis of symmetry at the center of the hemisphere.

4. The device of claim 1 wherein said inner surface has a white coating to reflect light.

5. The device of claim 1 wherein said light sources emit blue light.

6. The device of claim 1 wherein said openings with light sources are symmetrically distributed around said axis of symmetry.

7. The device of claim 1, further including a cover disposed on the side of the thread opposite said end face.

* * * * *